United States Patent [19]

Yamano

[11] 4,242,585
[45] Dec. 30, 1980

[54] DENTAL PANORAMIC RADIOGRAPHIC APPARATUS CAPABLE OF CONCURRENTLY TAKING NORMAL PICTURE OF TEMPOROMANDIBULAR JOINT

[75] Inventor: Hiroyoshi Yamano, Kawasaki, Japan

[73] Assignee: Kabushiki Kaisha Morita Seisakusho, Kyoto, Japan

[21] Appl. No.: 14,751

[22] Filed: Feb. 23, 1979

[30] Foreign Application Priority Data

Feb. 23, 1978 [JP] Japan .................................. 53/20642

[51] Int. Cl.³ ............................................. G03B 41/16
[52] U.S. Cl. .............................. 250/439 P; 250/413
[58] Field of Search ............... 250/439 P, 439 R, 451, 250/456, 491, 402, 413

[56] References Cited

U.S. PATENT DOCUMENTS

| | | | |
|---|---|---|---|
| 2,264,410 | 12/1941 | Schier | 250/451 |
| 3,849,649 | 11/1974 | Carey | 250/320 |
| 4,044,265 | 8/1977 | Schmidt | 250/439 P |

Primary Examiner—Craig E. Church
Attorney, Agent, or Firm—Koda and Androlia

[57] ABSTRACT

The disclosure relates to a dental panoramic radiographic apparatus capable of concurrently taking a normal picture of a temporomandibular joint in addition to a tomographic picture of a dental arch. The apparatus is highly significant in the photographic examination of a patient to be dentally treated in the jaw region, since the apparatus makes it possible to provide a tomographic picture of the dental arch and a normal picture of the temporomandibular joint simultaneously in the form of one sheet of X-ray film.

3 Claims, 11 Drawing Figures

(D)

(E)

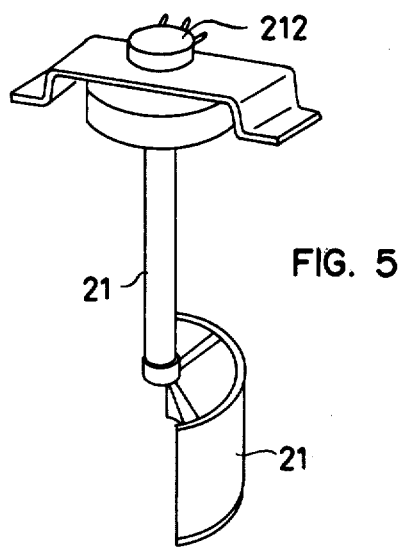
FIG. 5
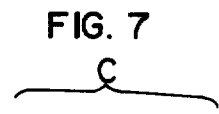
FIG. 7
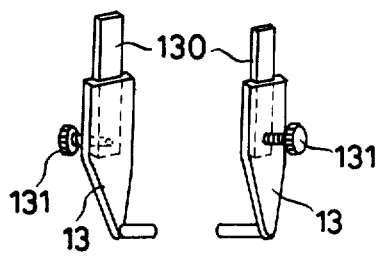
FIG. 6
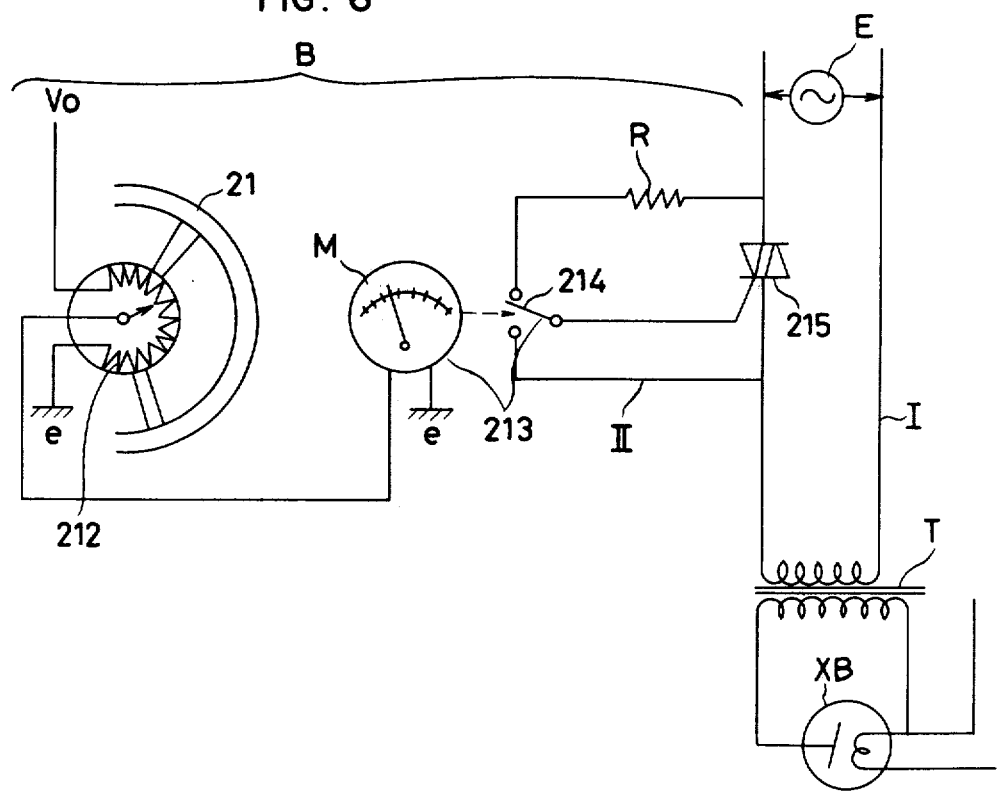

DENTAL PANORAMIC RADIOGRAPHIC APPARATUS CAPABLE OF CONCURRENTLY TAKING NORMAL PICTURE OF TEMPOROMANDIBULAR JOINT

BACKGROUND OF THE INVENTION

1. Field of the Invention

This invention relates generally to a dental panoramic radiographic apparatus and more particularly to an apparatus capable of concurrently taking a normal picture of a temporomandibular joint in addition to a picture of the tooth, jaw and face regions with one apparatus.

2. Prior Art

As well known, a conventional dental panoramic radiographic apparatus makes use of a curved plane section of an object. The apparatus panoramically pictures the entire jaw region and not only makes it possible to collectively diagnose individual and all the teeth and their ambient state of bone but also greatly contributes to a radiographic diagnosis of the face region such as an eye orbit, nasal cavity, otic cavity, etc. in addition to the tooth and jaw regions.

When medical treatment is given to a disease in the jaw region, it is an established fact from the viewpoint of dental examination of the disease that a dentist should have detailed information on the function and construction of a temporomandibular joint. For this reason, a normal radiographic picture of the temporomandibular joint is simultaneously taken in combination with the panoramic radiographic diagnosis mentioned above. As the method which has heretofore been practiced for taking a normal picture of the temporomandibular joint, there are provided various types of special photographing which use a panoramic radiographic apparatus commercially obtainable. But since all such types need special photographic attachments, special cassettes, etc. to be used with an existing apparatus, preparations by an operator for sets of such special photographic attachments, a particular posture of a patient to be pictured to correspond to the sets, and technique of photographing cause inconvenience to the operator and the patient. When comparing such inconvenience in the apparatus with the importance of examining the function of temporomandibular joint, the generalization of the use of the apparatus is not sufficient. In addition thereto, because the apparatus cannot picture a curved plane section of the temporomandibular joint, the temporomandibular joint and the other cranium constituting bones are overlapped and enlarged into one piece of X-ray picture, with the result that the picture disadvantageously becomes indistinct and lacks clearness.

SUMMARY OF THE INVENTION

Accordingly, this invention has for its object the removal of the disadvantages of the kind described above, and more particularly, the invention is intended to provide an apparatus capable of making an X-ray picture of a predetermined curved plane section of a temporomandibular joint in addition to an X-ray picture of a predetermined curved plane section of the tooth, jaw and face regions by applying comparatively simple additional means to a conventional panoramic radiographic apparatus capable of making an X-ray picture of a predetermined plane section of an object, namely, an apparatus capable of making the above two kinds of tomographic picture on one sheet of X-ray film by use of one radiographic apparatus. As will become apparent from a preferred embodiment of the invention, this invention makes it possible to provide an X-ray picture of an entire dental arch on the lower half or slightly larger half of one sheet of X-ray film and a normal picture made by the same apparatus of a predetermined plane section of the temporomandibular joint in an occlusal and a nonocclusal (open) state of the joint on the remaining upper part of the film, thus providing very convenient and accurate data for a dental examination. It is another advantage of this invention worthy of special mention that there is no such conventionally required particular conditions as for example a special attachment, specific cassette or the like by use of which a patient has to take a special posture with respect to the apparatus. In other words, essentially, the same method is employed as the conventional radiography in which a patient stands in front of the apparatus and that both an operator and a patient feel convenient such that the patient, after having had a normal X-ray picture taken of the tooth jaw and face regions, can keep his normal position and proceed to the next step of taking a temporomandibular joint picture.

A detailed explanation will now be made of a preferred embodiment of the invention with reference to the accompanying drawings.

BRIEF DESCRIPTION OF THE DRAWINGS

The above-mentioned features and objects of the present invention will become more apparent with reference to the following description taken in conjunction with the accompanying drawings, wherein like reference numerals denote like elements, and in which:

FIG. 5 is a perspective view of an essential part illustrating an example of an irradiation start-stop means for X-ray beams in the apparatus of the invention;

FIG. 6 is a principle diagram; and

FIG. 7 is a perspective view of an essential part showing an example of a fixing and holding means for positioning the head of a patient used in the apparatus.

DETAILED DESCRIPTION OF THE INVENTION

Figure 1:
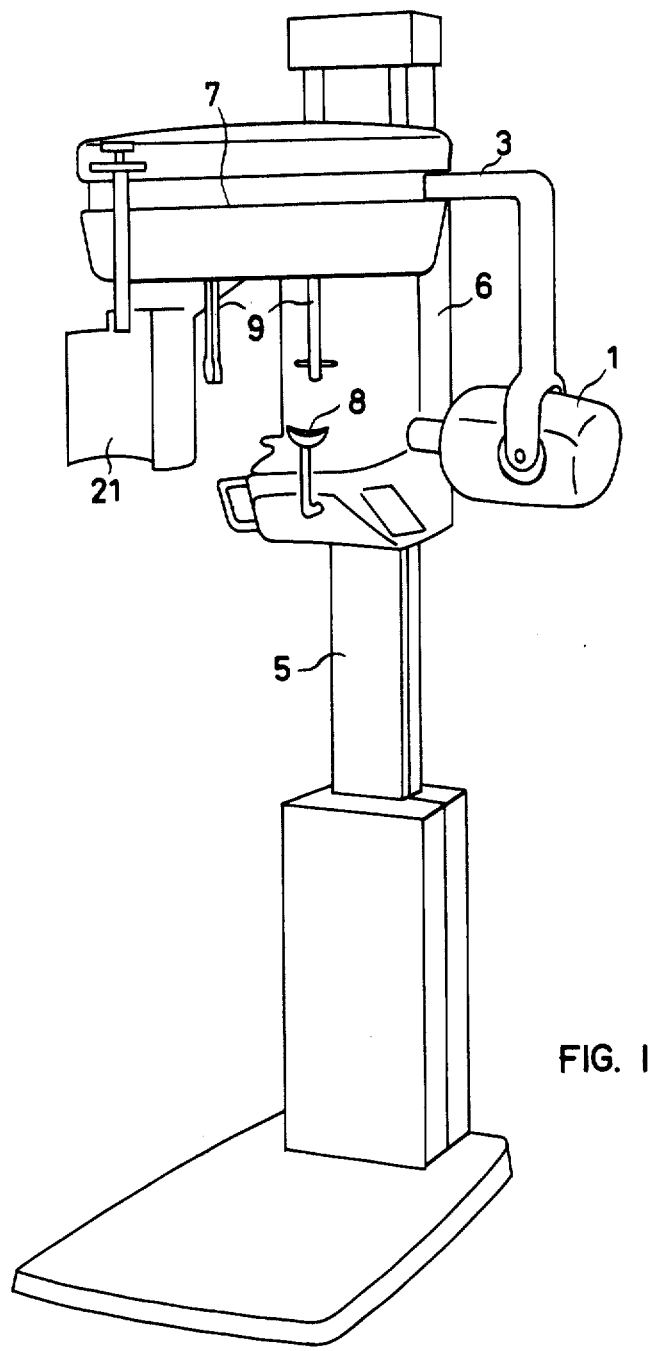
FIG. 1 is a schematic front view of the panoramic radiographic apparatus.
Figure 4:
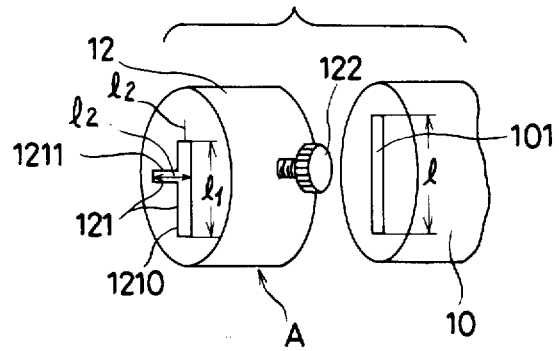
FIG. 4 is a schematic perspective view showing an example of an X-ray film length adjusting means in the apparatus of the invention.

As shown in FIG. 1, the body of the panoramic radiographic apparatus of the invention is made by adding two or three means to the conventional apparatus and these means are later described. The general appearance of the apparatus of the invention is not essentially different from the conventional apparatus as shown in FIG. 1. Namely, the numeral 5 in FIG. 1 designates a support, and a support base 6 is elevatable by a suitable means (not shown) with respect to the support 5, and a body 7 and an arm 3 are fixed to the base 6. To one end of the arm 3 is fixed an X-ray source 1 and to the other end is fixed a film holder 21. Inside the body 7 are contained a means (not shown) for moving the holder 21 around the arm 3 and a means (not shown) for simultaneously moving the X-ray source 1 and the holder 21 around the jaws of a patient with respect to each other. A chin rest 8 is suspended from the base 6 and a pair of ear rods 9 and 9 are suspended from the body 7. The radiographic apparatus of the construction described above is well known from the apparatuses commercially obtainable, for example, as trademark "PANEX" from Morita Seisakusho and from other makers. According to the invention, the following additional means are attached to such conventional type of apparatus. The first of the means is a means A for adjusting the longitudinal axial length of X-ray beams 11 from the X-ray source 1, and this means A is made up of a cylinder cap 12 fixed rotatably to a header 10 of the X-ray source 1 as shown in FIG. 4. In front of the cap 12 are provided an adjusting slit 121 for cutting the height of a vertical slit 101 of the header 10 within the desired range and an operating knob 122 for turning the cap 12 in the circumferential direction of the header 10. The cap 12 is preferably mounted inside the header 10, but may be mounted outside the header 10, depending upon circumstances. The adjusting slit 121 is shown as a cross slit consisting of a first slit 1210 which cuts the upper part of the height l of the slit 101 by $l_2$ and a second slit 1211 which is normal to the slit 1210 and measures $l_2$ in overall length. The cross slit is adapted to permit the beam adjustment of the cylinder 12 in two ways, namely, in a corresponding relation with respect to the header 10 shown in FIG. 4 and in a position normal to the corresponding relation, and it will be understood that the slit 121 can suitably be increased or decreased in number and size, depending upon how long the slit 121 should be made in length. The present applicant filed previously Japanese Utility Model Application No. 176,989/76 for one type of construction of the adjusting means A. It is apparent that the length of longitudinal axis of X-ray beams 11 irradiated from the slit 101 is controlled in accordance with the slit 121 by the use of such means. A second means B is a means for starting and stopping the irradiation of X-ray beams 11 in any position of a predetermined plan section of an object, and the means is adapted to make an X-ray picture of only the specified or restricted point of one piece of film 2 by automatically starting and stopping the irradiation of X-ray beams with respect to the specified (desired) range, when the film holder 21 is rotating along with the rotation of the arm 3 in the process of radiographic operation. The means B shown as an example in FIGS. 4 and 5 comprises a potential divider 212 rotating in a coaxial relation with the shaft 211 of the film holder 21 and producing electric potential corresponding to the rotated position, a detection member 213 for operating a switching element 214 in the range of specified voltage of the divided potential of the potential divider 212, and a switching element 215 adapted to open and close the power circuit 1 for X-ray source 1 in an interlocking relation with the switching element 214. More particularly the potential divider 212 represents a potentiometer having specified pilot voltage applied thereto, the detection member 213 represents a meter relay (namely, a voltmeter M and relay switch 214), and the switching element 215 represents a triac which interlocks with the relay switch 214 for closing and opening a gate circuit II inserted in series into the power circuit I and led out in parallel by the power circuit I. The reference character e in FIG. 6 designates ground; R a resistor; T a transformer; XB an X-ray tube; and E designates an X-ray power source. The means B described above functions in the following manner.

When the film holder 21 is rotated, potential corresponding to each position of rotation of the holder 21 is produced by the potentiometer 212. Supposing that a meter relay 213 is set in the manner that the relay 213 is caused to read divided potential in the above each position of rotation in the form of the value indicated by a meter pointer and to close the switch 214 in the specified range of the pointer (in the range of voltage) and open the same in other ranges, the power circuit I is closed only when the gate circuit II is closed by the switch 214, and the gate current of triac 215 is shut off when the gate circuit is opened. As a result, the power circuit I is opened and that X-ray beams is irradiated only in the specified position of the film holder 21 and is stopped in other positions of the holder 21.

Another additional means C of the invention is a means for fixing and holding the head 41 of a patient 4 in a position above or below the position in which to photograph the jaw region. Referring to the means C in comparison with the conventional ear rods 9 and 9, the only modification that is necessary for the conventional rods 9 was to accommodate the individual differences in the ear holes of a patient through up-and-down motion of the ear rods 9 and 9 in the relaxed upright position in which the patient placed his chin securely on the chin rest 8, whereas as will become apparent from the way of photographing to be described hereinafter, the invention is constructed in a manner that the ear rods 13 and 13 of the invention can attain that range of up-and-down movability which was not imparted to the conventional ear rods 9 and 9. Namely, after the patient has finished having his dental arch photographed, the ear rods 13 and 13 are enabled to adjust the height of the rods to correspond to the position of his ear holes when the patient takes any of postures higher in an upright position and lower in a stooped position than the posture he took when he had his dental arch photographed. The adjusting rods 130 and 131 which operate in this manner are shown in FIG. 7 in the form of base rods 130 around which the ear rods 13 are slidably inserted and adjusting bolts 131 for fixing the ear rods 13 to the adjusting rods 130 in the specified position.

Figure 2:
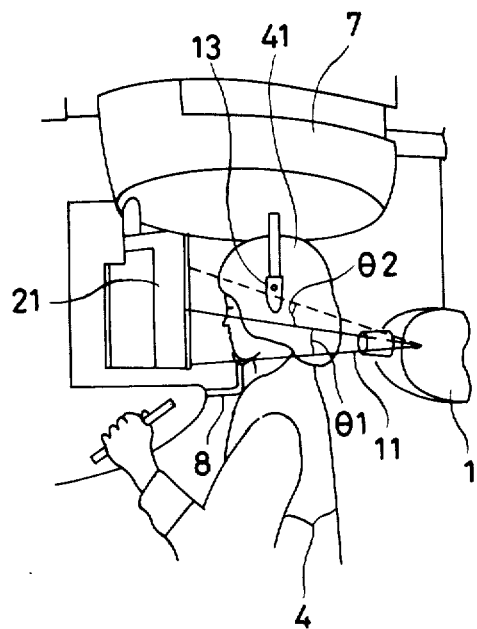
FIG. 2 shows a procedure taken for photographing by use of the apparatus of the invention wherein FIG. (A) shows photographing of a dental arch in a still state, (B) shows normal photographing of a temporomandibular joint (left) in an occluding state, (C) the same normal photographing (right), (D) normal photographing of the temporomandibular joint in a nonoccluding state (open state) (left), and Figure (E) shows the same photographing (right)
Figure 2:
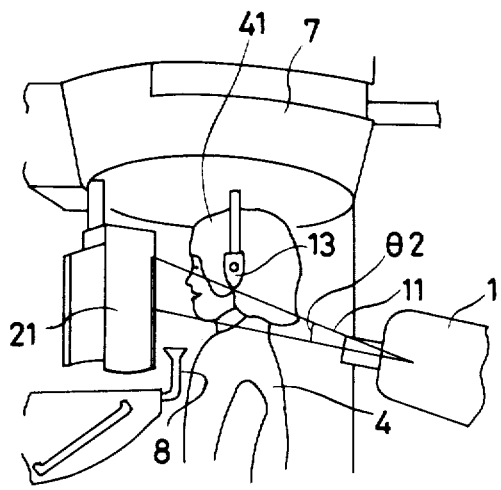
Figure 2:
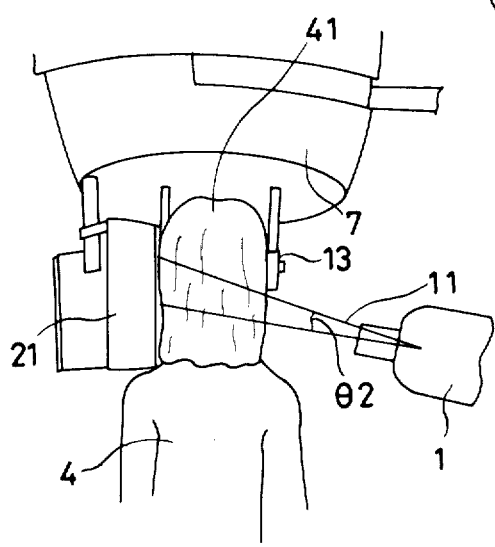
Figure 2:
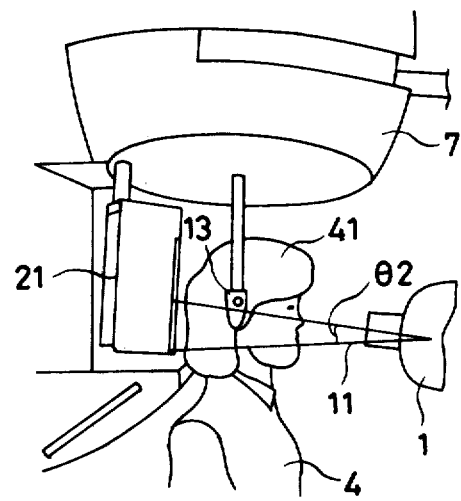
Figure 2:
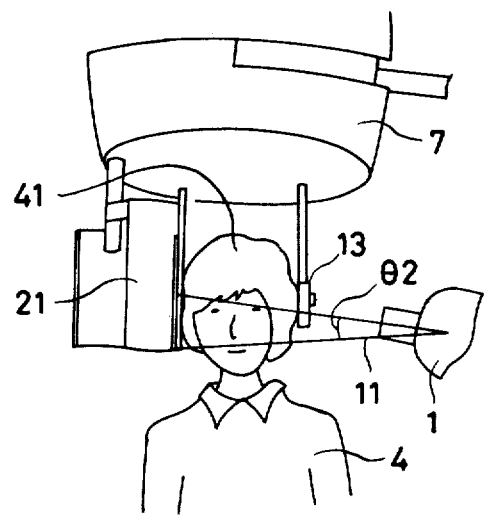
Figure 3:
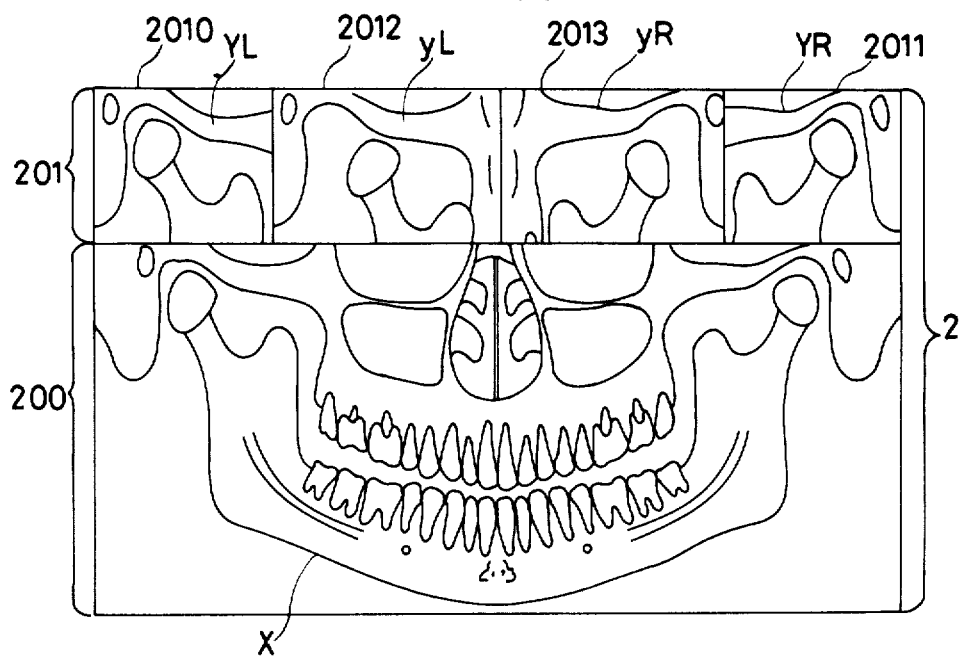
FIG. 3 is a top plan of X-ray film obtained by photographing in FIG. 2.

A description will now be given of the procedures both for making an X-ray picture of a curved plane section of a dental arch and for making a normal X-ray picture of a temporomandibular joint by use of the apparatus of the invention with respect to FIGS. 2(A) through 2(E) and 3 showing an embodiment of the invention. FIG. 2(A) shows normal photographing of the dental arch of a patient in a still position, and in the invention, the relation between the X-ray source 1, X-ray, film holder 21 and the patient 4 is the same as in the conventional apparatus except that the angle of irradiation of X-ray beams 11 is cut to an extent of the upper side $\theta_2$ to form an angle $\theta_1$. It should be understood that cutting of the above angle of irradiation $\theta_2$ is carried out by the first slit 1210 of the means A described above with reference to FIG. 4 corresponding to the slit 101 (namely, by the fact that angle $\theta_1$ is obtained by $l_1$). Tomogram Y of the entire dental arch in the lower area 200 alone in FIG. 3 is continuously obtained by this photographing, and the remaining upper area 201 of the film 2 is left unexposed. Next, in the case where there is a space between the head 41 of a patient 4 and the body 7 when the patient 4 detach his chin from the chin rest 8 and takes a natural upright position (namely, in the case where the patient is relatively short in stature), a normal picture is taken of the left occluding temporomandibular joint in the range of angle of irradiation $\theta_2$ from X-ray source 1 as seen in FIG. 2(B) (this angle of irradiation $\theta_2$ is obtained by moving the second slit 1211 by 90° upward in the righthand part of FIG. 4) and a normal picture is taken of the right occluding temporomandibular joint by moving the X-ray source 1 and film 2 as shown in FIG. 2(C). These right and left plane section images of blocks 2010 and 2011 alone in the upper area 201 of film 2 in FIG. 3 are discontinuously (sporadically) projected as YL and YR but other parts are not projected. To this end, the means B described with reference to FIGS. 5 and 6 is used and X-rays are irradiated by the means B only when the blocks 2010 and 2011 in the area 201 of film 2 correspond to the X-ray source 1, and irradiation of X-rays is stopped in other parts of the area 201. When the patient 4 is long in stature such that he strikes the head 41 against the body 7 in an upright position, photographing is carried out by inverting the film as shown in FIGS. 2(D) and (E). Namely, film 2 is taken out from the holder 21 after a tomogram has been made of the dental arch and, then the film 2 is inverted and reloaded into the holder 21 and is exposed in the manner that irradiation of X-ray beams from the X-ray source 1 comes within the range of lower side $\theta_2$ (this angle $\theta_2$ is obtained by moving the FIG. 2 slit 1211 down by 90° in the lower lefthand of FIG. 4). By this photographing, it is possible to take a normal picture of the occluding temporomandibular joint with respect to blocks 2010 and 2011 alone out of the area 201 of film 2 in the same way as described with reference to FIGS. 2(B) and (C). It will be understood that when the patient is long in stature, the manner of photographing in FIGS. 2(D) and (E) is significant in that it may form the cause for which an X-ray operator becomes inaccurate in photographing to raise the X-ray source 1 and the film holder 21 in accordance with his stature. Following the above photographing, a normal picture is taken of the right and left jaw joints in an opened state, and the procedure for this photographing is the same as the preceding procedure described with reference to FIGS. 2(B) (C) or (D) (E). But these images YL and YR are projected on the block 2012 (left jaw) and block 2013 (right jaw) in the area 201 of film 2. As earlier described, X-ray beams are irradiated by the application of the means (B) only when the blocks 2010 and 2011 of film 2 are caused to correspond to the X-ray source 1. Accordingly, in order for the images YL and YR to be projected on the blocks 2012 and 2013 respectively, it is necessary to forcefully move the film 2 inside the holder 21 either to the left or to the rightside by a manual or other means so that the block 2012 may move to the position of the block 2010 and the block 2013 may move to the position of the block 2011 during the process of photographing. Namely, for example, in either of the FIGS. 2 (B) (C) and (D) (E) procedures, if the film 2 is manually moved to the left inside the holder 21 to the amount of the pitch of block 2010 before the X-ray source 1 corresponds to the left temporomandibular joint, a tomographic picture is taken of the block 1012 when the source 1 has come to correspond to the left temporomandibular joint. In the case of the right temporomandibular joint, it is only necessary to reverse the preceding procedure, namely, to move the film 2 to the right to the amount of the pitch of block 2011. It will become apparent from the above procedures for photographing that the invention renders it possible to make a normal picture of the entire dental arch and the occluding state and nonocculuding state of right and left joints on a sheet of film 2. It should be understood that, in the above process of photographing, the employment of the means C for fixing and holding the head 41 of a patient 4 makes it possible to take the same quality pictures of the patient as often as are necessary.

As described above, the apparatus of the invention is highly useful for the photographic examination of the tooth and jaw regions of a patient to be dentally treated in that the apparatus makes it possible for one apparatus to produce a normal picture of a temporomandibular joint together with the tooth and jaw regions on a sheet of film by additionally providing an existing X-ray apparatus for photographing the tooth and jaw regions (and in addition, the face region not shown) with a means A for adjusting the longitudinal axial length of X-ray beams, a means B for starting and stopping the irradiation of X-ray beams in any position of plane section of an object, and a means C for fixing and holding the head of a patient above or below the position for photographing the tooth and jaw regions. Also, because the invention makes it possible to take a radiographic picture of the curved plane section of a temporomandibular joint, not only is the picture obtained high in clarity but also no mounting of any special additional member or cassette, nor taking of any particular posture for photographing is necessary for a dental X-ray operator, nor any change in the position of the patient for having a picture taken, nor taking any special posture by the patient is required for the patient. All that is necessary for the dentist to do is to follow the same procedure for photographing as that for taking an X-ray picture of the tooth and jaw regions. Thus, the invention makes it possible not only for dentists but also medical X-ray technicians, patients, and X-ray apparatus makers to secure material benefits from the invention.

It should be apparent to those skilled in the art that the above described embodiment is merely illustrative of but only one of the many possible specific embodiments which represent the application of the principles of the present invention. Numerous and varied other arrangements can be readily deviced by those skilled in the art without departing from the spirit and scope of the invention.

I claim:

1. A dental panormaic radiographic apparatus capable of concurrently taking an X-ray picture of a tooth and jaw region and of a temporomandibular joint of a patient comprising a rotatable arm, an X-ray source provided on one end of said arm, an X-ray film provided on another end of said arm opposing said X-ray source and moving in synchronism about a patient's head with said X-ray source when said arm rotates with a constant distance being maintained between said X-ray source and film, said apparatus being characterized in that said apparatus comprises a means for fixing and holding a head of a patient in a position for photographing said tooth and jaw regions and a position above or below the position for photographing said tooth and jaw regions for photographing said temporomandibular joint and a means for starting and stopping the irradiation of an X-ray beam from said X-ray source in any of a plurality of positions as said arm rotates, said starting and stopping means comprising a means for sensing rotational position of said arm which generates a voltage which varies with the rotational position of said arm and a switching element which interrupts and connects a power source to said X-ray source in response to said varied voltage.

2. A device according to claim 1, further comprising a means for adjusting the height of said X-ray beam.

3. A dental panoramic radiographic apparatus capable of concurrently taking an X-ray picture of tooth and jaw regions and of a temporomandibular joint of a patient comprising a rotatable arm, an X-ray source provided on one end of said arm, an X-ray film provided on another end of said arm opposing said X-ray source and moving in synchronism about a patient's head with said X-ray source when said arm rotates with a constant distance being maintained between said X-ray source and film, said apparatus being characterized in that said apparatus comprises:

a means for adjusting the longitudinal length of said X-ray beam;

a means for fixing and holding the head of a patient in a position for photographing said tooth and jaw regions and a position above or below the position for photographing the tooth and jaw regions, said means for fixing and holding comprising height adjusting means capable of making a pair of ear rods correspond to the ear holes of a patient when the rods are above or below the posture of the patient, placing his chin on a chin rest, said rods being a pair of right and left ear rods suspended from a body; and a means for starting and stopping the irradiation of an X-ray beam at any position of a predetermined plane section of an object, said starting and stopping means comprising a potential divider, said divider moving in a coaxially relation with a shaft of a film holder to correspond to the position of the movement thereof, a detection member for operating a first switching element in a specified voltage range of divided potential of said potential divider, and a second switching element for closing and opening a power circuit for said X-ray source in response to said first switching element.

* * * * *